US008207863B2

(12) United States Patent
Neubauer et al.

(10) Patent No.: US 8,207,863 B2
(45) Date of Patent: Jun. 26, 2012

(54) GEOMETRICAL PROPERTIES MEASURING DEVICE FOR A MEDICAL TREATMENT DEVICE INCLUDING AN RFID TRANSPONDER

(75) Inventors: Timo Neubauer, Poing (DE); Norman Plaβky, Erfurt (DE); Manuel Millahn, München (DE)

(73) Assignee: Brainlab AG, Feldkirchen (DE)

( * ) Notice: Subject to any disclaimer, the term of this patent is extended or adjusted under 35 U.S.C. 154(b) by 653 days.

(21) Appl. No.: 11/851,444

(22) Filed: Sep. 7, 2007

(65) Prior Publication Data

US 2008/0068197 A1    Mar. 20, 2008

Related U.S. Application Data

(60) Provisional application No. 60/826,973, filed on Sep. 26, 2006.

(30) Foreign Application Priority Data

Sep. 15, 2006 (EP) ..................................... 06019346

(51) Int. Cl.
    *G08B 21/00* (2006.01)
(52) U.S. Cl. .................. 340/686.1; 340/572.1; 606/1
(58) Field of Classification Search ............... 340/572.1, 340/572.4, 572.7, 686.1; 600/587, 424; 606/1
    See application file for complete search history.

(56) References Cited

U.S. PATENT DOCUMENTS

| 6,351,659 B1 | 2/2002 | Vilsmeier |
| 7,166,114 B2 * | 1/2007 | Moctezuma De La Barrera et al. .............................. 606/130 |
| 7,362,228 B2 * | 4/2008 | Nycz et al. .................. 340/572.1 |
| 2002/0143268 A1 | 10/2002 | Meredith et al. |
| 2006/0025668 A1 * | 2/2006 | Peterson et al. .............. 600/407 |
| 2006/0129140 A1 | 6/2006 | Todd et al. |

FOREIGN PATENT DOCUMENTS

| DE | 196 39 615 | 4/1998 |
| WO | 97/29678 | 8/1997 |
| WO | 97/29710 | 8/1997 |
| WO | 01/54558 | 8/2001 |

OTHER PUBLICATIONS

Summons from Oral Proceedings for European Application No. 06019346.3 dated Sep. 1, 2009 and response to summons.

* cited by examiner

*Primary Examiner* — Jeffery Hofsass
(74) *Attorney, Agent, or Firm* — Renner, Otto, Boisselle & Sklar, LLP (57) ABSTRACT

A measuring device for measuring geometric properties of a medical treatment device includes a measuring unit, a time detection unit, and an RFID writer. The measuring unit is configured to measure a relative position between at least a first part of the medical treatment device and at least a second part of the medical treatment device. The time detection unit configured to detect a time of the measurement, and the RFID writer configured to write a time, based on the detected time, to an RFID transponder of the medical treatment device.

8 Claims, 5 Drawing Sheets

GEOMETRICAL PROPERTIES MEASURING DEVICE FOR A MEDICAL TREATMENT DEVICE INCLUDING AN RFID TRANSPONDER

RELATED APPLICATION DATA

This application claims priority of U.S. Provisional Application No. 60/826,973 filed on Sep. 26, 2006, which is incorporated herein by reference in its entirety.

FIELD OF THE INVENTION

The present invention relates to a device and method for measuring geometric properties of medical treatment devices. More particularly, the invention relates to automatically verifying, calibrating and surveying instruments for use in computer-assisted surgery, wherein the geometry of the instrument and of a reference system can be ascertained as a three-dimensional model with the aid of optical scanning methods.

BACKGROUND OF THE INVENTION

In computer-assisted operations, the position and orientation of surgical instruments relative to the patient's anatomical structures can be represented to the surgeon with the aid of a navigation system (e.g., on a display device of the navigation system). In addition to the anatomical structures, the instruments used during the medical procedure may be tracked using suitable reference devices (also referred to as reference systems), such as marker means. These reference systems include, for example, active or passive marker structures, and can be used to identify a position in three-dimensional space to a medical navigation system by emitting or reflecting, for example, infrared radiation.

In a registration process, the anatomical structures can be initially correlated with reference systems mounted thereon via navigable pointers. Thus, the structures can be tracked by the navigation system during the medical procedure.

The same is true for the instruments and their reference systems (e.g., marker means), wherein instrument-typical functional elements may be tracked. The functional portions can include, for example, surfaces of tools (e.g., cutting edges, tips, etc.) that may be used, for example, to treat bone structures. In using such instruments, the surgeon may employ a navigation system to obtain precise information concerning the position and orientation of the bone structures, even when visibility is impaired. The spatial position of the instrument and its functional elements can be represented on a display device, wherein the representation can be based on a correlation of stored geometric data of the instrument and the spatial data (which can be ascertained by the navigation system via the reference device attached to the instrument). When the stored geometric data, which mainly describe the functional elements of the instrument in relation to the reference device, deviate from the actual geometry of the instrument (e.g., after the instrument has been damaged), then an incorrect representation of the relationship between the actual instrument and the anatomical structure to be treated may be produced. This is particularly true if the information stored in the database concerning the initial outline of the instrument continues to be used.

Typically, the relationship between the functional element of the instrument and its reference device is defined once on the basis of manufacturing documents. Compliance of this relationship can be ensured by surveying the instrument and reference device after the manufacturing process. The relationship can be stored in the navigation system and retrieved during or before subsequent operations. These so-called pre-calibrated instruments (e.g., bore guides) are occasionally verified pre-operatively using navigable aids to confirm that they are dimensionally accurate. If they are not sufficiently dimensionally accurate, a message can be displayed to the user indicating that the instrument is out of calibration.

Matching model data to the possibly defective instrument is not possible in verification. The precision that verification may achieve is inevitably dependent on the precision of the navigation system, since the respective reference devices are again correlated with each other. Visibility problems and occasionally poor manageability when simultaneously positioning the instrument and the aid tend to extend the operation time.

In another method, a calibration procedure of the instrument may be carried out before the instrument is used. In this method, the values of functionally relevant parameters of the instrument (length, diameter, ... ) used during navigation but still unset, or unset values for assigning the reference device to the functional element (e.g., socket driver with variable sockets) or the deviations of the actual instrument from the model stored in the database are determined by means of a navigable calibration tool. The calibration tool may be temporarily or permanently stored in the navigation system and utilized as needed. Here, too, the visibility and manageability problems described above have a negative effect on the operation time. Calibration functions well for instruments having functional elements with simple geometries, but again only within the limits of the precision that the navigation system can achieve.

Completely surveying functionally relevant structures of an instrument that is difficult to calibrate or verify represents a third calibration method. However, this method is not currently employed since suitable aids are not available, nor could the required procedures be carried out within a reasonable time frame.

Marker means that represent examples of a reference systems can be detected by means of a detection means (e.g., a camera or ultrasound detector). Such detection systems are also referred to as navigation systems and used in IGS (image-guided surgery). The marker means typically include three markers that are arranged in a fixed and predetermined location relative to each other and are in particular mechanically linked. The markers can be passive or active markers, wherein passive markers reflect signals (e.g., waves and/or radiation) emitted in their direction, and active markers are themselves the origin of the signals (e.g., radiation and/or waves). The signals emitted by the (active or passive) markers, which can be wave signals or radiation signals, are detected by a detection device (e.g., a camera). In order to establish a position of the marker means relative to the detection means, the marker means is preferably moved to provide the detection means with various views of the marker means. On this basis, the location of the marker means relative to the detection means can be determined in a known way, in particular in a spatial reference system. Reference is made in this respect to DE 196 39 615 A1 and the corresponding U.S. Pat. No. 6,351,659, which are hereby incorporated by reference in their entirety.

Instrument calibration can lose its validity in the course of time. In particular, the geometric properties of the medical treatment device can change in the course of time. This can be caused by attrition or by being mechanically burdened once or repeatedly.

SUMMARY OF THE INVENTION

A method and device for verifying, calibrating and surveying instruments for computer-assisted surgery are advantageously provided. The method and device provide increased reliability in processes and time reduction when employing navigated instruments for surgical procedures. Applicability of the device and method is not limited to symmetrical or otherwise geometrically simple navigable instruments, but rather instruments with complex geometries can be prepared for use in computer-assisted surgery.

The device and method described herein generally relates to measuring devices and measuring methods for measuring geometric properties of a medical treatment device, in particular an instrument with or without a reference system, or of a reference system for an instrument (e.g., a marker means that can be linked to an instrument). Verifying, calibrating and/or surveying the medical treatment device represent an example of measuring the geometric properties of the medical treatment device. A geometric property of a medical treatment device, for example, can be the relative location between at least a first part of the medical treatment device and at least a second part of the medical treatment device, wherein the second part differs from the first part. The first part can be a functional element of the instrument, e.g. an instrument tip, and the second part can be a grip or handle of the instrument or a marker means attached to the instrument. The first part also can be a first marker sphere of a marker means, and the second part can be a second marker sphere of the marker means.

The location of the above parts is preferably determined by the position of the parts in a predetermined reference system. The reference system preferably is a reference system in which a detection means (e.g., camera) or the measuring device (e.g., scanning unit) lies. The positions, for example, can be described using Cartesian coordinates or spherical coordinates. The location of one part (e.g., the first part) relative to another part (e.g., the second part) can be described by spatial angles, distances, coordinates (in a reference system) and/or vectors and is preferably calculated from the positions describing the location. These positions can be calculated, for example, by means of a program running on a computer.

The term "relative location" used herein or the expression "location of a part A relative to a part B" includes the concept of the relative positions between the two parts.

The time of measurement of the geometric property can be detected and written to an RFID (radio-frequency identification) transponder by means of an RFID writer. An example of an RFID transponder is an RFID label, an RFID chip or an RFID tag. The RFID writer can be located, for example, in the medical treatment device. When reading the RFID transponder, it is possible to determine how much time has elapsed since the last calibration and thus how reliable the calibration data may be. The older the calibration, the more likely it is that the measured geometric properties are no longer valid. It is thus all the more urgent to request re-calibration.

The time detection unit, for example, can be a clock (in particular a radio-controlled clock) that is preferably coupled to the measuring unit and receives signals from the measuring unit. The time detection unit, for example, receives a signal when the measuring unit begins measuring, when the measuring unit is in the process of measuring, and/or when the measuring unit has completed measuring the geometric property or geometric properties of the medical treatment device. The time detection unit then establishes the time at which this signal was received. The time can be detected with varying precision. The time of day, for example, can be determined to the hour, to the minute or to the second. It is also possible to determine only the date, e.g., the day, month and year, or only the week and the year, or the month and the year. Imprecisely detecting the time is tolerable when a geometric property that is typically stable over a long period of time, for example years, is expected for the medical treatment device.

A system for implementing the methods described herein can include the measuring device in conjunction with a medical treatment device. The RFID transponder used in the medical treatment device can be one that includes a rewritable memory. In this way, it is possible, when re-surveying the medical treatment device, to write the current time of measurement to the RFID transponder.

The measuring device preferably is configured such that the RFID writer obtains measurement data from the measuring unit. The RFID writer, for example, can be signal-linked to the measuring unit or to a data processing means that processes the measured data. The RFID writer can be configured to also write measurement data from the measuring unit to the RFID transponder of the medical treatment device, in addition to the detected time.

The measuring unit measures at least the relative location between a first part of the medical treatment device and a second part of the medical treatment device. This means that a more comprehensive measurement (such as a calibration) in which the location of a large number of parts of the medical treatment device can be determined relative to each other can be performed. The measuring unit can be configured as a so-called pointer (e.g., a pointer comprising at least two marker spheres) that is observed by a camera system, in particular a navigation system, during the sensing procedure. In the sensing procedure, parts of the medical treatment device can be tapped by means of the pointer. The relative location between the parts can be determined from the observation signals.

The measuring unit can be configured as a scanning unit that detects the geometry of an instrument including a reference device attached thereto. The device can further include a data processing unit that, for example, is configured to calculate a three-dimensional model of the instrument (e.g., with the aid optical scanning methods) based on the detected geometry of the instrument and of the reference system. The model then can be used by the navigation system. Other example functions of the data processing unit are described below.

The measuring device can include a data processing means that calculates an index time from the detected time, e.g., the time of measurement. The index time can be understood as an expiry time of the medical treatment device. Once a period of time has expired after measurement of the geometric properties, it may be the case that the geometric properties are no longer valid; in particular, there may be an increased risk that the geometric properties are no longer valid. If this period of time is added to the time of measurement, this results in the aforesaid index time. The index time can vary depending on the type of instrument surveyed. The data processing means therefore preferably includes a database in which, depending on the type of instrument, various periods of time (index periods of time) are stored. Once these time periods have elapsed or expired, it is assumed that the geometric properties of the medical treatment device are no longer valid. The time that is written to the RFID transponder by means of the RFID writer can thus be the aforesaid measurement time and/or the index time.

The type of the medical treatment device, for example, can be input by a user or can be determined by means of the measurement data based on the typical geometric data of the medical treatment device or based on a model ascertained on the basis of the measurement data. This can be a three-dimensional model such as is described further below in connection with surveying. The type of the instrument surveyed thus can be automatically determined. In particular, various models of the medical treatment devices (instruments and/or reference systems) can be stored for this purpose. It is therefore possible to automatically determine the type of the medical treatment device, wherein the data concerning the determined type are written to the RFID transponder, in conjunction with the determined time (time of measurement and/or index time). The RFID writer, which preferably is coupled to the data processing means, thus also can write the determined type of the medical treatment device to the RFID transponder (e.g., in addition to the time data and measurement data).

A navigation system can be used in conjunction with or to implement the methods described herein, where the navigation system enables a medical treatment device to be navigated. The navigation system can include the data processing unit described above, wherein the navigation system preferably includes an RFID reader/writer that is operative to read or otherwise retrieve the time stored in the RFID transponder and also to write data to the RFID transponder. The navigation system can be configured such that the retrieved time is compared with the index time. If the retrieved time is after the index time, the navigation system can carry out an index-time-exceeded operation. This index-time-exceeded operation can include, for example, emitting a warning signal that warns the user that the geometric properties of the treatment device have not been measured, in particular not calibrated, for some time. There is therefore an increased risk that the navigation system is using data concerning the geometric properties of the medical treatment device, in particular calibration data, which are no longer valid. Alternatively or additionally, the index-time-exceeded operation can be configured such that navigation using the medical treatment device is inhibited. This is in particular advantageous when the manufacturer of the medical treatment device only guarantees that the geometric properties are maintained for a certain period of time. The navigation system preferably includes a data processing unit, for example, that controls and/or carries out the comparative operation and/or index-time-exceeded operation described herein.

If a medical treatment device is re-surveyed, in particular re-calibrated, using the measuring device, then the RFID transponder of the medical treatment device is preferably retrieved, as stated above. Preferably, both the detected time and the previously measured geometric properties are retrieved. The data processing unit then can compare the retrieved geometric data from the RFID transponder with the newly measured data. If these data differ by a predetermined amount, then an index time at which re-measurement should be carried out can be defined as being after a period of time that is shorter than the period of time between the last measurement and the current measurement. If the newly measured geometric properties do not differ from the geometric properties stored in the RFID transponder, then an index time can be set to be after a period of time that is equal to or longer than the period of time between the last measurement and the current measurement.

In the navigation system, the data concerning the geometric properties, stored in the RFID transponder, can be used to navigate, in particular to three-dimensionally represent, the medical treatment device.

The RFID transponder can be located in the interior of the medical treatment device or can be attached to an exterior portion of the treatment device. An RFID chip, for example, can be integrated in the interior, or an RFID label can be attached onto the surface of the medical treatment device.

The reference system, which can be embodied as a marker means, also can include the RFID transponder, as an alternative or in addition to the RFID transponder of the instrument. The RFID transponder of the marker means can contain characteristic data of the marker means, in particular the location of the markers (e.g., marker spheres) relative to each other (which is characteristic of a marker means).

Verifying, calibrating and surveying by means of the measuring device advantageously serves to provide correct instrument data with respect to the geometry of the functional elements and the reference device or system (e.g., marker means) and their relation to each other as well as to the navigation system. Preferably, this information is provided before the operation is begun and temporarily or permanently stored in the memory of the navigation system. Then, an intra-operative application of verifying, calibrating and surveying can be implemented so as to enable reuse of instruments that have been deformed. The navigation system can be configured to retrieve the data directly from the RFID transponder of the medical treatment device.

The instrument data can contain specifications regarding the position of the functional elements of the instrument (e.g., instrument tip) in relation to a reference device, which may be fixedly attached or detachable from the instrument and formed from markers (active or passive technology). The data also can specify how the functional elements, such as for example the tips of the instrument, are shaped.

In the methods described herein, the geometry of the instrument (including a mounted or mountable reference device or system formed from at least two markers) can be ascertained by means of a scanning device or sensing device that preferably operates without contact. The ascertained geometry then can be compared with previously stored values that can be clearly assigned to the instrument or group of instruments, and/or is newly stored if surveyed. In particular, the reference device or system can be permanently arranged on the instrument or can be temporarily attached thereto (e.g., during the scanning procedure). The surface data of the instrument gained by scanning then can be converted into a three-dimensional model of the instrument by means of a data processing unit or computing unit. Based on model, the instrument-typical parameters can be calculated. The three-dimensional model of the instrument can contain information utilized for navigation, including the geometry of the instrument's functional elements and reference system and their relation to each other. The geometric information concerning the instrument can be transferred to the navigation system to enable the surgeon to use the instrument in computer-assisted surgery.

The precision and therefore speed of the example scanning process is decisively controlled by the information which is already available and accessible for this instrument, wherein at least one verification, or for that matter a calibration or even a complete survey of the properties of the instrument, can or even has to be carried out. Measuring devices and methods are described below.

Measuring Unit

The scanning device, which can be either integrated in the navigation system or accommodated in a separate enclosure, is an example of a measuring unit. The scanning device can use known 3D scanning techniques such as, for example, split beam methods or object screen methods, which use a screened instrument surface. Alternatively, the scanning device can use grid projection methods wherein telecentric grids are projected onto the instrument's surface. The scanning unit located in the scanning device preferably operates optically, such as by means of a laser, wherein the surface of the instrument (including the permanently or detachably mounted reference system having at least two markers) is sensed. The instrument to be scanned then can be mounted in an instrument holder contained in the scanning device. During the scanning procedure, this instrument holder can be moved or rotated relative to the scanning unit in order to make the instrument of the scanning unit accessible from all sides, thereby enabling a complete digitization of the surface. Alternatively, the scanning unit can move or rotate relative to a fixed instrument holder. In both cases, the movement or rotations can be detected or controlled via suitable sensor technology integrated in the scanning device so as to enable correlation of the angular positions with the scanning results, whereby a realistic 3D model can be calculated.

An emission model and/or reflection model of the active and/or passive markers forming the reference system also can be determined during the scanning procedure by means of an infrared camera unit. The camera unit can be provided separately or can be contained in the scanning device, and the position of the camera unit in relation to the scanning unit can be fixed and known or can be ascertained. The information thus ascertained concerning the markers' radiation properties, depending on the angle of observation and the resulting optical outline (which may be detected by the navigation system as the spatial position of the reference system) can be correlated with the results from the determination of its geometric outline (by means of a scanning process). Thus, observation errors of the navigation system that can result from the changing visibility properties of the markers in certain positions, e.g., through partial damage to the markers, can be compensated for during use (e.g., during an operation). This can increase the representation precision of the instrument's position in relation to the anatomical structure to be treated on the display device of the navigation system. In other words, misinterpretations of the spatial position of the reference system occurring, for example, due to damaged markers, can be compensated for by the camera unit of the navigation system in the subsequent navigation procedure, and the realistic position of the instrument, in particular of the functional element(s), in relation to the anatomical structure can be calculated and represented.

Data Processing Unit

The measuring device can include a computing unit or data processing unit. The data, detected by the scanning unit, concerning the geometry of the navigable instrument, for example, can be transmitted to and further processed in the data processing unit. For example, the data processing unit can calculate a three-dimensional model of the instrument, including the reference system, from the results of the surface scan. Preferably, the data processing unit can evaluate the captured data or the three-dimensional model produced, such that the geometry of the instrument's functional elements (e.g., tips) and their position in relation to the reference system of the instrument can be ascertained.

Database

The device can further include a database that can be linked to the data processing unit, such that data input into the data processing unit or transmitted to the data processing unit can be stored in the database. For various instruments, information concerning the geometry of the functional units and of the instrument's reference device or system, and their position in relation to each other, can be stored in the database (e.g., under the control of the data processing unit). Further, information concerning the quality of the markers or the properties of the emission model and/or reflection model of the instrument-specific reference device or system also can be stored in the database. Geometric properties of various types of instruments and/or reference systems can be stored, such that the type of instrument or reference device/system can be determined from the measured geometric properties.

Display Device

A display device, such as a screen that communicates via a wire connection or wirelessly (e.g., WLAN, Bluetooth, etc.) with the data processing unit and the user interface unit, also can be provided in the measuring device. The ascertained information concerning the geometry of the functional elements of the instrument and of its reference system, and their position in relation to each other, can be represented graphically or numerically. Preferably, the three-dimensional model of the instrument, retrieved from the database or ascertained by processing the scanning results, is displayed on the display device, wherein the model is substantially represented on the display device. The realistic representation of the three-dimensional model on the display device allows the user to transmit commands for performing the methods described herein. Further, a user interface, which can be arranged on the display device (e.g., a touch screen), enables the user to provide commands and data to the data processing unit. If, after having been introduced into the scanning device, the instrument is incorrectly recognized or simply not recognized, the user commands can control the selection of the correct model from a plurality of similar model variants. Furthermore, the graphic representation of instruments hitherto unknown to the scanning device, after a rough scan, can be used to interactively select the areas of the instrument required for successfully preparing the instrument for surveying, in particular the functional elements and the reference system. Designations also can be input for new instruments, making the instruments easier to subsequently locate in the database.

Navigation System Connection

The navigation system also can be linked wirelessly or via a wire connection to the measuring device or the data processing unit, such that the information, ascertained in accordance with the methods described herein, concerning the geometry of the functional elements and of the reference system of the instrument, and their position in relation to each other, and also the quality of the active and/or passive markers and their resulting emission model and/or reflection model, can be transmitted to the navigation system, in particular to its database. By means of the information, the navigation system can assist the surgeon in carrying out computer-assisted surgery, by providing the previously or just ascertained or most current instrument-specific data. As stated above, the navigation system preferably captures the data or a part of the data from the RFID transponder of the medical treatment device, such that a data link between the navigation system and the measuring device is not always necessary.

Method for Automatically Verifying, Calibrating and Surveying Navigable Surgical Instruments The method for navigable surgical instruments and associated time detection is described below with its exemplary steps and operating sequences.

In verification, the geometric data of the instrument can be previously stored in a database of the navigation system, as is typical for so-called pre-calibrated instruments. Verifying these instruments can include checking whether the stored data match the actual geometry, in particular the shape of the functional elements, and their relation to the reference system. Omitting the verification step can lead to the medical procedure being carried out with an instrument that is damaged, but not necessarily obviously so, which can result in the present position of the instrument being incorrectly represented by the navigation system in relation to the anatomical structure.

Preferably, the navigation system can identify the instruments on the basis of the characteristic and differentiable spatial arrangement of the markers forming the reference system. Once recognition is successful, this enables the instrument-specific data to be retrieved from the database for further use during navigation.

Since the scanning device for carrying out verification can (but need not) be located in the camera system's field of vision, identification with the aid of the navigation system cannot therefore necessarily be ensured. Therefore, it is occasionally useful to also suggest other identification procedures that enable the scanning device to systematically retrieve the instrument data. Automatically verifying navigable surgical instruments can involve identifying an instrument by means of a barcode, NFC (near field communication) or preferably RFID (radio frequency identification). In such methods, the information media can be automatically detected by the scanning device or, if the instrument is within the data capture range of the navigation system, by the navigation system, when inserting the instrument into the scanning device. These mobile information memories can contain the geometric data of the instrument and, associated with them, the time of capture of the geometric data. The mobile memory also can provide the necessary instrument information, on the basis of which it is possible to quickly locate both the instrument-specific data and the associated time data in the database of the navigation system. It is furthermore conceivable for the user to select the instrument to be verified, using a suitable, in particular graphic interface which can be represented either with the aid of the display device of the navigation system or via a display device belonging to the measuring device (e.g., scanning device). The information concerning the instrument, used for locating the geometric data stored in the database, also can be transferred to the measuring device (e.g., scanning device) via a manual input, e.g., by means of an instrument identification code. Verification is also possible by carrying out an initial scan or rough scan at a reduced level of detail after the instrument has been inserted into the scanning device. The scan can be used to ascertain a model of the instrument at a low or reduced resolution or a rough structure of the instrument in a very short time, wherein the model or structure enables a search for the instrument by comparison with instrument models stored in the database. Here, too, once the search is successful, the complete instrument data stored in the database of the navigation system can be retrieved and used in the subsequent verification. It is also possible, after the rough scan of the instrument, to carry out a fine scan or a further or second scanning procedure of the instrument or parts of the instrument at a higher or increased level of detail, from which a model at a high or higher resolution or a detailed or more precise structure can be ascertained.

For all the described verification embodiments, it is advantageous, after identifying the instrument, to scan at least the functional elements and the reference device or system of the instrument, in particular their shape und position in relation to each other, at a high level of detail so as to obtain sufficiently precise data for comparing the geometry stored in the database with the actual instrument geometry. A recognition logic then can be used that independently identifies the characteristic instrument elements so as to define an instrument reference device or system on the basis of the markers forming the reference device or system. Then, the position of the functional elements with respect to the reference device or system can be ascertained. When using passive spherical markers, for example, identifying the reference system is ensured by their easily recognizable shape, which otherwise occurs rather infrequently in surgical instruments. Instruments with active markers (which can be linked to an energy source during the scanning procedure if detecting the emission model is desired) can also be formed with geometrically larger characteristic shapes in order to more easily locate the geometrically small diodes in their vicinity (using the recognition logic, once a rough scan has been performed). When using an external energy source linked by cables, the recording device preferably is embodied to be spatially fixed, while the scanning unit moves relative to it.

If the verification result is positive (e.g., the instrument is identical to the stored model within a given tolerance level), this can be transmitted to the navigation system via a suitable data link (via a wire connection, wirelessly) and the instrument can be activated for the subsequent application.

Calibration

Automatically calibrating navigable surgical instruments is substantially the same in its method sequence to verifying as described above. In verification, only one assertion is made concerning the similarity of the model and the actual instrument, which, if deviated from beyond or to a greater extent than the permitted tolerance level, excludes the instrument from then being employed in navigation. When calibrating, the geometric information of the instrument stored in the navigation system's database is corrected such that the instrument is scanned in the areas beyond the permitted tolerance levels and the results are transferred into the database of the navigation system as updated model data.

Surveying

In surveying, geometric data of the instrument need not be previously stored in a database of the navigation system. Further, the instrument need not be known to the navigation system or to the scanning device. Automatically surveying, as in the procedure described above, begins by mounting the instrument to be surveyed, equipped with passive or active markers, in the instrument holder of the scanning device. The instrument then can be scanned to ascertain a three-dimensional model of the instrument, or an initial scan or rough scan can be performed at a reduced level of detail or low resolution.

After the scan, a rough three-dimensional model of the instrument or an instrument model at a low resolution can be calculated with the aid of the data processing unit and then represented to the user on the display device. By using the recognition logic to locate characteristic shapes, e.g., geometric shapes forming the reference system, the scanning device, after a first evaluation of the geometric data of the initial scan, can provide suggestions to the user for defining the markers forming the reference system and the functional elements of the instrument, e.g., using colored or other such distinctions. The user can confirm the suggestions or make improvements with the aid of the user interface unit which is preferably embodied as a touch screen. The data processing unit can use these specifications to define the scanning area for the subsequent or second scanning procedure, which can be carried out in the defined areas of the instrument's functional elements and reference device or system at high or increased precision or resolution.

The obtained surface information then can be transmitted via a wire connection or wirelessly to the data processing unit, which can calculate the exact geometric values for the position of the markers forming the reference system and their distance from the instrument's functional elements (e.g., tips). The instrument-specific parameters thus determined can in turn be transmitted wirelessly or via a wire connection to the database of the navigation system which, when recognizing the characteristic reference geometry formed by at least two active or passive markers, can retrieve the corresponding information concerning the position of the functional element from the database.

In order to subsequently verify or calibrate the instrument, it is conceivable to store the instrument geometry in the database under a name input by the user via the user interface unit, in order to simplify subsequent location of the data. A mobile data memory that may be mounted on the instrument and may use RFID (radio frequency identification) technology can be used. The geometric information used for subsequent verification or calibration, to be carried out on other measuring devices, thus can be stored on and/or retrieved from the instrument. In particular, the time of measurement can be stored on and/or retrieved from the instrument.

Result of Measuring, in Particular Automatically Verifying, Calibrating and Surveying Instruments for Computer-Assisted Surgery Once navigable surgical instruments have been automatically measured, in particular verified, calibrated and/or surveyed, in conjunction with the time detection with which the time of measurement is detected, the spatial position of the instrument's reference device or system, formed from at least two active or passive markers, can be determined with the aid of the navigation system. The instrument can be identified from the characteristic position of the markers in relation to each other, a complete model of the instrument (including the reference device or system and functional elements) can be retrieved from the database of the navigation system, and/or its position in relation to the anatomical structure to be treated can be precisely represented to the surgeon on the display device of the navigation system.

Also provided is a computer program which, when loaded onto a computer or running on a computer, carries out the methods as described above, and a program storage medium or a computer program product comprising such a program.

BRIEF DESCRIPTION OF THE DRAWINGS

The forgoing and other features of the invention are hereinafter discussed with reference to the drawing.

DETAILED DESCRIPTION

Figure 1:
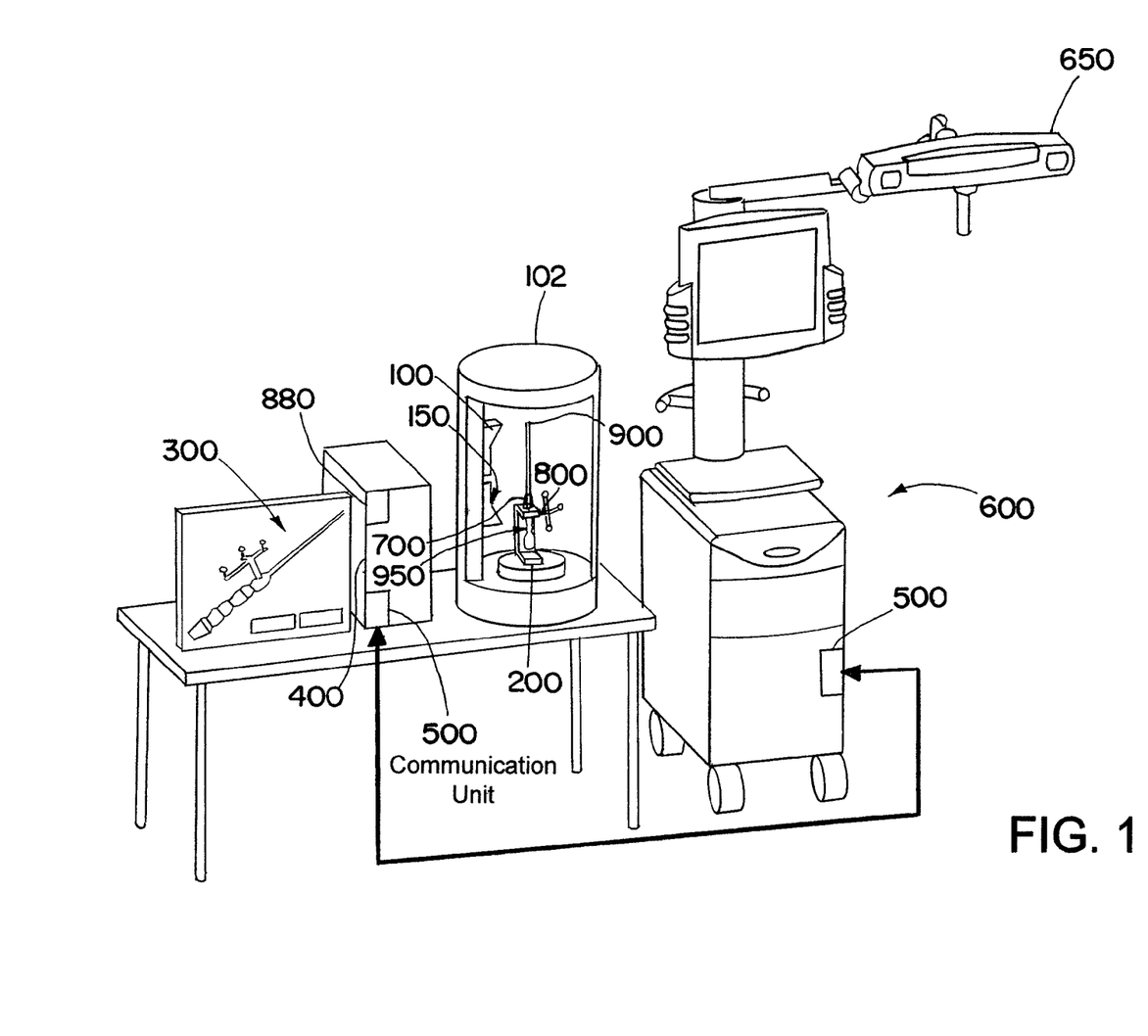
FIG. 1 illustrates an exemplary device in accordance with the invention for automatically verifying, calibrating and surveying an instrument, wherein the exemplary device includes a separate display device and a separate data processing unit.

FIG. 1 illustrates an exemplary embodiment in accordance with the present invention, wherein a scanning device 100 and an instrument holding unit 200 are arranged in a cylindrical casing 102. An infrared camera unit 150 also can be attached in the casing 102 in order to check the condition, shape or quality of active or passive markers. The check can be performed, for example, by emitting infrared radiation onto the markers and, via the infrared camera unit 150, detecting the reflected infrared radiation. Alternatively, the infrared camera unit 150 can detect infrared radiation emitted by the markers. In the present example, an instrument 700 is positioned within the casing 102, preferably fixedly or non-movably in the instrument holding unit 200, wherein a reference system 800 is attached to the instrument 700 and the instrument 700 comprises an instrument tip 900 as a functional element. An RFID transponder 950 is located in the interior of the instrument 700 and/or the reference system 800.

The scanning device 100 preferably optically senses the instrument 700, for example, by means of a laser, or tactilely, wherein the casing 102 of the scanning device 100 can be open, as shown in FIG. 1, or also closed. The scanning device 100 or the laser of the scanning device 100 also can perform a rotation about the instrument 700. Alternatively, the scanning device 100 or the casing of the scanning device 100 can be formed such that a rotation of the instrument holding unit 200 or of the instrument 700 can be performed and the shape of the instrument 700 can be detected from all sides. The casing 102 of the scanning device 100 can have a size at which conventional medical instruments can be positioned in the casing 102 of the scanning device 100 and preferably can be completely scanned or sensed. The infrared camera unit 150, which in the present example is attached in or to the casing 102 of the scanning device 100, can examine the quality (including the uniform reflection properties) of the markers, for example by the infrared camera unit 150 irradiating the markers from various angles and by ascertaining the condition or quality which the markers exhibit from the reflection characteristics of the markers. Thus, for example, uniform reflection properties of the markers can indicate a good or intact condition or a high quality of the markers, while non-uniform reflection properties or non-uniform reflection characteristics, detected by the infrared camera unit 150, can indicate a damaged condition or low quality of the markers.

From the quality ascertained or the condition or shape of the markers or reference system 800, detected for example from various angles of observation by means of the infrared camera unit 150, the optical outline of the reference system 800 or of the markers can be calculated. The optical outline then can be combined with the ascertained information concerning the geometric outline of the reference system 800. The correlation of the optical and geometric outlines can be used to compensate for errors by a camera 650 of a navigation system 600 during navigation (depending on the angle of observation of the reference system) due to the spatial position being incorrectly calculated, for example because of damaged markers.

The detected information concerning the instrument 700 and the reference system 800, which is preferably arranged on the instrument 700 during the scanning procedure, and the position or quality of the markers can be transmitted from the scanning device 100 to a data processing unit 400 in which the captured scanning data are converted into a virtual model. The data processing unit 400 can recognize or ascertain functional elements or functional units of the instrument 700, for example directly from the captured data concerning the geometry of the instrument 700 and the reference system 800. Alternatively, the data processing unit 400 can ascertain the corresponding functional elements, taking into account the geometric relations of the instrument 700 such as the characteristic arrangement of the markers forming the reference system 800, for example, by comparing the ascertained geometric relations with the geometric relations stored in a database.

The database, in which the comparative values or comparative geometric relations or newly ascertained geometric relations can be stored, can be arranged in the data processing unit 400. The virtual three-dimensional model of the instrument 700, calculated by the data processing unit 400, or the ascertained information concerning the geometry of the instrument 700 and the reference system 800, can be displayed or graphically represented on a display device 300, such as a touch screen. In particular, various alternative shapes or geometries of the instrument 700 or of the functional elements of the instrument 700 also can be displayed, the shape or geometry of which may be similar to the ascertained geometries or functional units of the instrument. From these shapes, a user can select an instrument 700 or a functional element.

The information ascertained, such as the geometric relations of the instrument 700 and the reference system 800 or the virtual model of the instrument 700, can be transmitted from the data processing unit 400 to the navigation system via a wire connection or wirelessly, such as by means of WLAN or Bluetooth, via a communication unit 500. The communication unit 500 can be arranged on the data processing unit 400 and navigation system 600, such that a navigation procedure can be carried out by the navigation system 600 on the basis of the ascertained information concerning the geometry of the instrument 700. In the navigation procedure, the ascertained information concerning the geometry of the instrument 700 and the reference system 800 can be taken into account, and information concerning the condition or quality of the markers can also be taken into account, such that damage to the markers or changes in the geometry or damage to the instrument, for example, can be taken into account in the navigation procedure so as to guarantee a precise navigation procedure.

A time detection unit 880 can detect the time of measurement. The time detection unit 880 may be implemented via software executed by data processing unit 400, for example. Alternatively, the time detection unit 880 may be implemented by a hardware circuit included within or separate from the data processing unit 400. The detected time can be transmitted directly to the RFID reader/writer, which then writes the time data to the RFID transponder. Alternatively, the time detection unit 880 can pass time data first to the data processing unit 400, which then transmits the time data to the RFID reader/writer. Still further, the time data can be transmitted to the navigation system 600.

Figure 2:
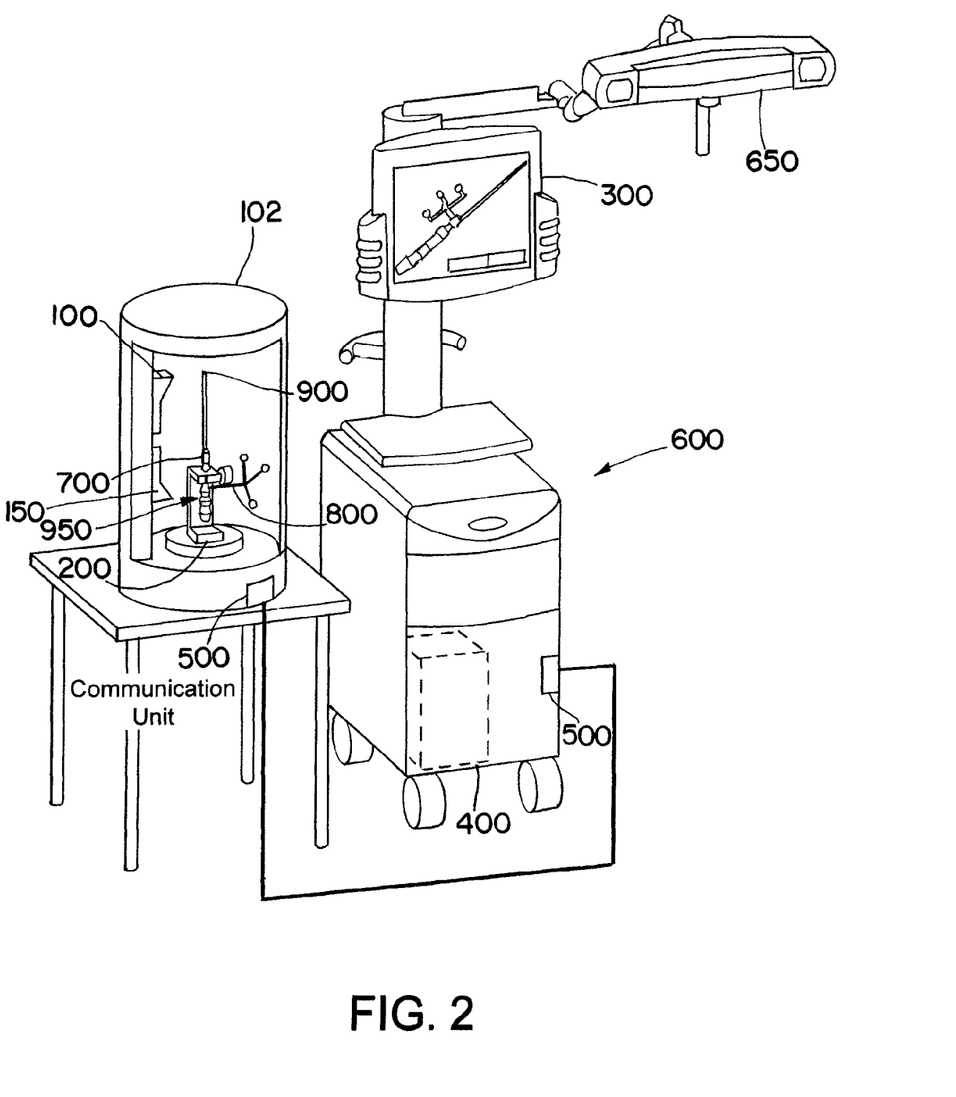
FIG. 2 illustrates another exemplary device in accordance with the invention for automatically verifying, calibrating and surveying an instrument, wherein the exemplary device includes a display device attached to a navigation system, and a data processing unit integrated into the navigation system.

FIG. 2 shows another exemplary embodiment in accordance with the present invention, wherein the data processing unit 400 and/or the display device are integrated into the navigation system 600 and/or arranged in/on the navigation system.

Figure 3:
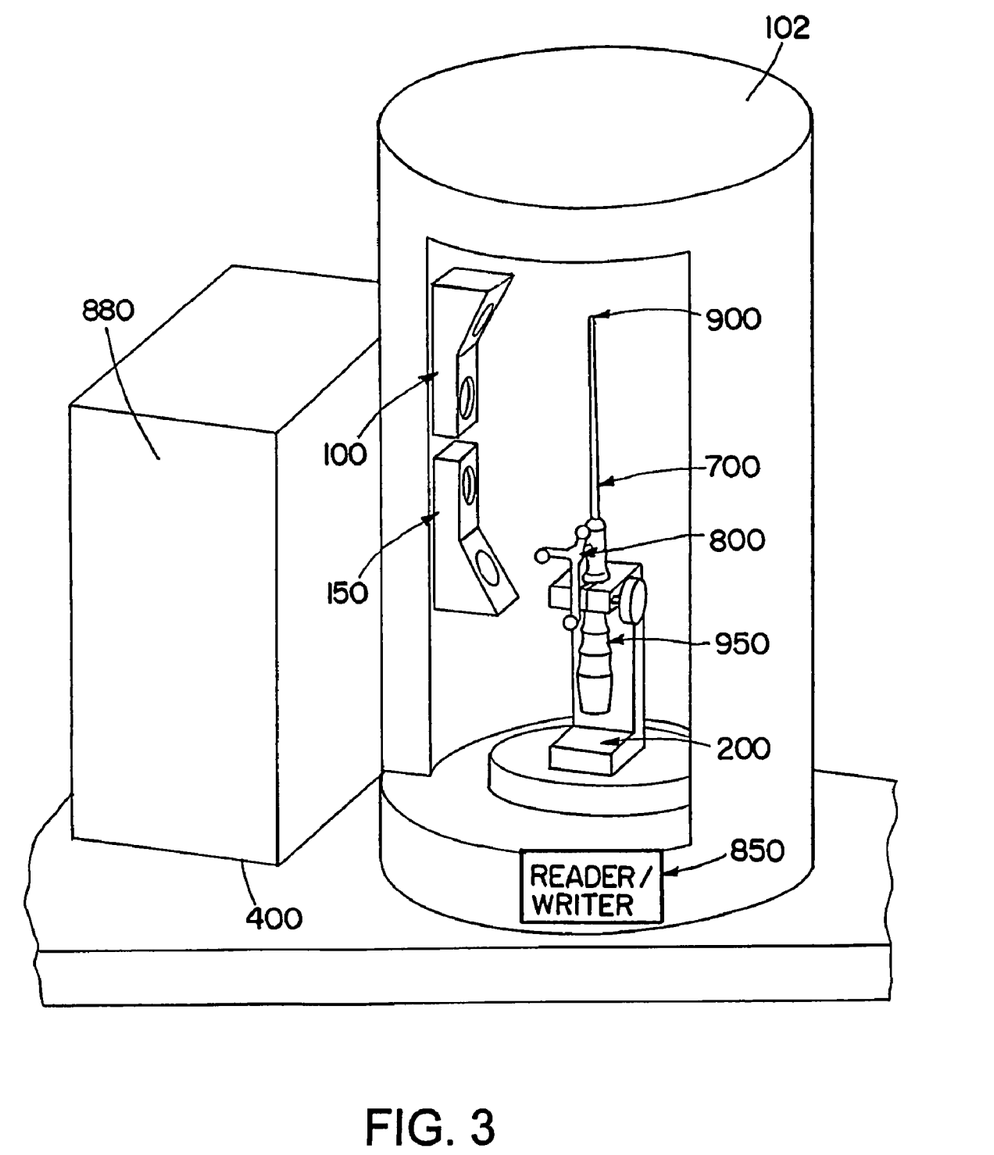
FIG. 3 illustrates an exemplary scanning device in accordance with the invention, wherein an instrument is placed within the scanning device.

FIG. 3 shows a casing 102 (e.g., an enclosure) of the scanning device in which the instrument 700 is positioned, comprising a scanning unit 100, an infrared camera unit 150 and an instrument holder 200 (the instrument is shown in the instrument holder and preferably fixed to the holder). The instrument 700 has an instrument tip 900 as a functional element, the shape of which, for example, can be detected by the scanning unit 100. A reference system 800 also is arranged on the instrument 700, the shape of which, for example, can be detected by the scanning unit 100. The reference system 800 is formed by markers, for example, the reflection characteristics of which can be detected by the infrared camera unit 150. In the example shown, the RFID transponder 950 is located in the hand grip of the instrument. The data stored in the RFID transponder 950 are read by the RFID reader/writer 850.

Figure 4:
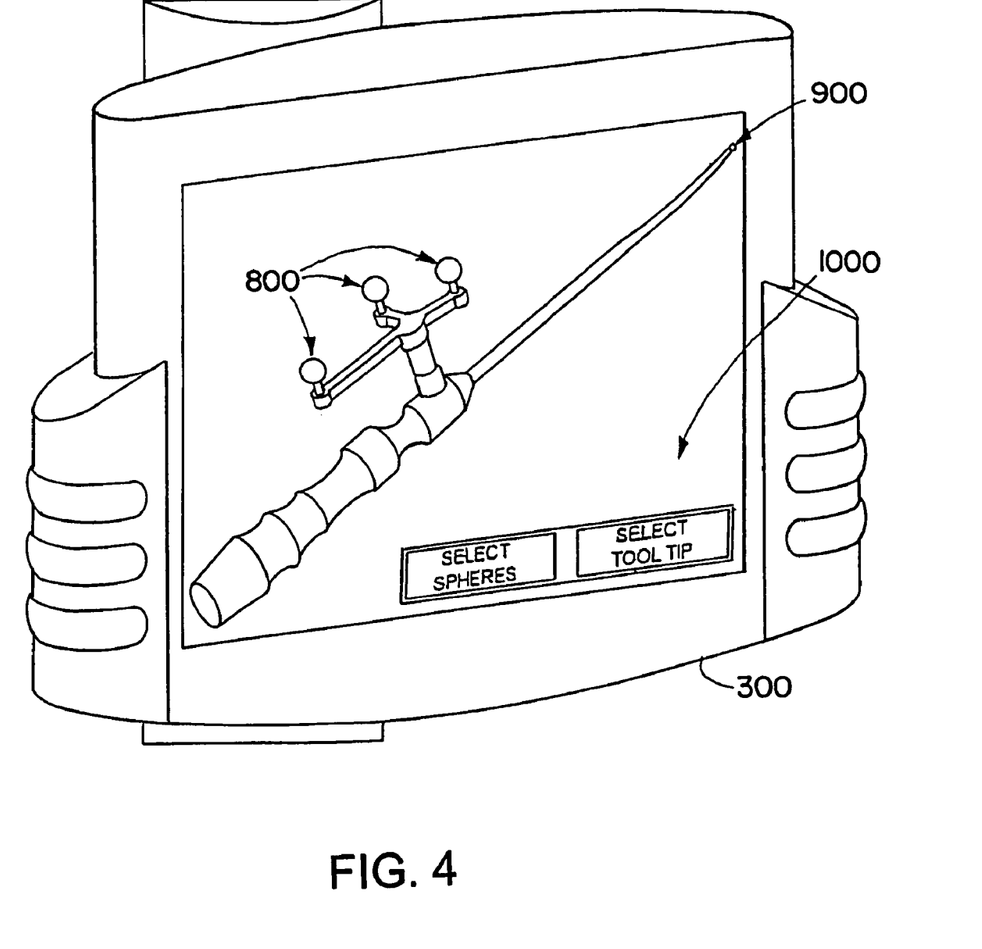
FIG. 4 illustrates an exemplary display device in accordance with the invention.

FIG. 4 illustrates an exemplary display device 300 that graphically represents the virtual ascertained three-dimensional model of the instrument 700 together with the reference system 800. By means of a user interface unit 1000, preferably arranged on the display device 300, the markers or functional elements, such as the tip 900 of the instrument 700, for example, can be selected by a user.

Figure 5:
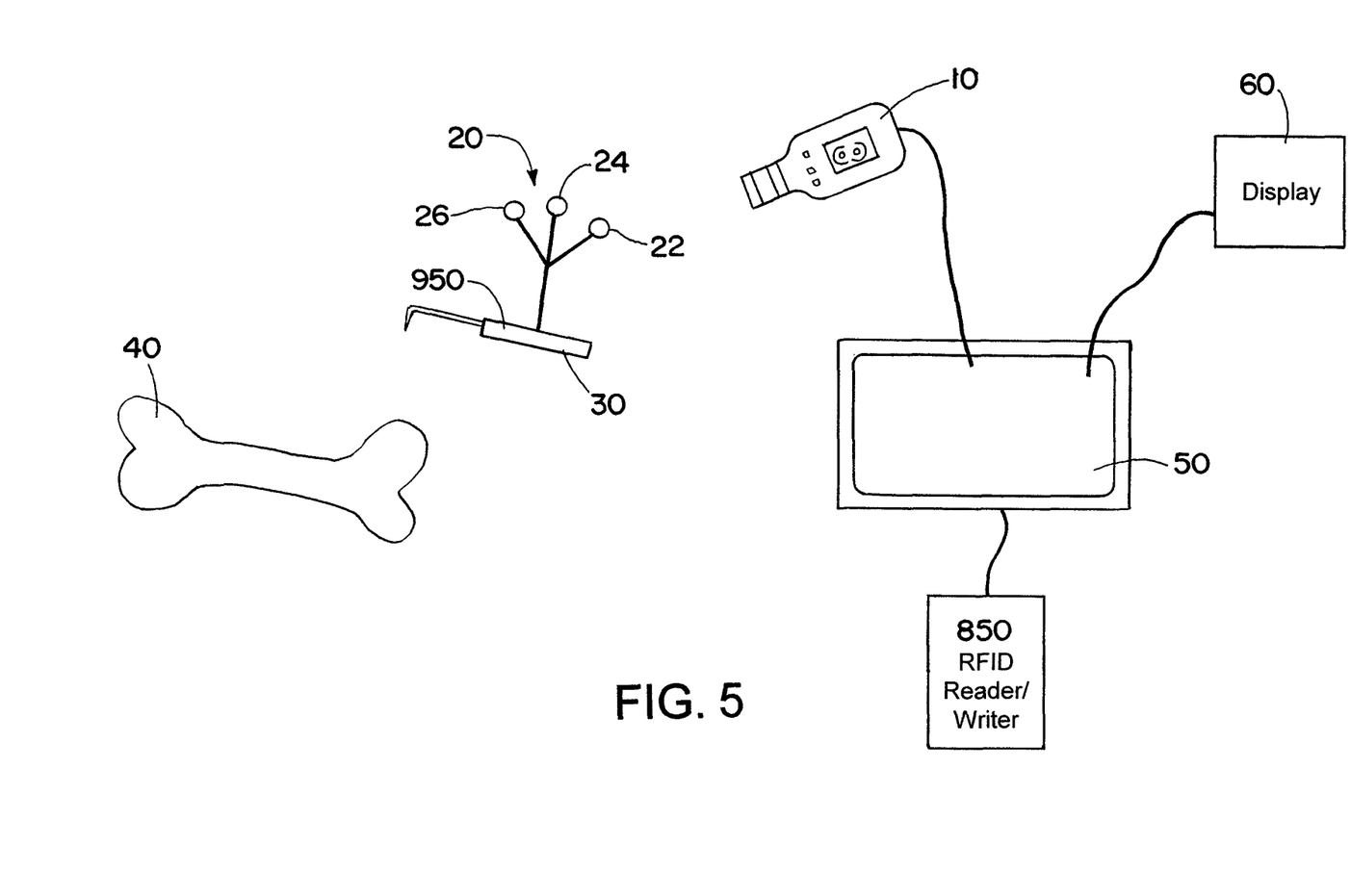
FIG. 5 illustrates an exemplary navigation system in accordance with the invention.

FIG. 5 illustrates an exemplary navigator (e.g., a navigation system) including a camera 10 for detecting a marker means 20 comprising marker spheres 22, 24, 26. The marker means 20 preferably is configured as a reference star. The reference star 20 is attached to an instrument 30 for treating a body structure 40, e.g., a patient's bone. The reference star 20, together with the instrument 30 (e.g., a knife) form a medical treatment device. The marker spheres can be passive or active and can be detected by the camera 10, which represents an example of a detection means. The detection signals from the camera 10 can be transmitted to a data processing means 50.

An RFID transponder 950 that can be read by an RFID reader/writer 850 can be located in the instrument 30. The reader 850 can be coupled to the data processing means 50 in order to transmit the read data to the data processing means 50. The read data preferably include data concerning the geometric properties of the instrument 30 and/or the reference star 20. The RFID transponder 950 can be linked to the instrument 30 or the reference star 20, e.g., attached onto it or located in its interior.

The read data preferably include the geometric properties of the instrument 30 and/or the reference star 20. The data also contain time data representing the time of measurement of the geometric properties. The data also may contain data that describe the type of the instrument 50 and/or the reference star 20. All these data are preferably read by the reader 850 and transmitted to the data processing means 50.

The data processing means 50 calculates an index time, up to which the data for the geometric properties are valid, from the time of measurement. The index time may also be referred to as an expiry date.

The aforesaid index time can be stored in the RFID transponder 950 of the medical treatment device 30, as an alternative or in addition to the time of measurement, e.g., the data processing means 50 used to measure the geometric properties of the medical treatment device 30 calculates the aforesaid index time from the measured time at which the geometric data are measured by means of the measuring device, and said index time then is written to the RFID transponder 950 of the medical treatment device by means of the RFID writer.

If the index time, which also may be referred to as an expiry time, is stored in the RFID transponder, then it can be read by the reader 850 shown in FIG. 5.

An index time thus can be calculated in the data processing means 50 and/or received from the reader 850. The index time is preferably compared with the current time. If the index time is before (earlier than) the current time, an index-time-exceeded operation is preferably carried out, wherein for example a warning signal is represented on the display means 60. The display means 60 can serve to represent the position of the instrument 30. Alternatively or additionally, the representation of the instrument 30 on the display 60 can be prevented, for example, by switching the display 60 off under the control of the data processing means 50. Alternatively or additionally, a warning tone signal can of course be emitted as a warning signal.

As stated above, an identification code also can be read from the RFID transponder 950, said code specifying the medical treatment device. If the data processing unit 50 calculates the index time, it can do so depending on the identified instrument. To this end, the data processing means 50, for example, refers to a database that defines, for various types of instruments, different validity time periods from the measurement time the geometric properties. This is useful, since different medical treatment devices exhibit different mechanical stability and are subjected to a different typical burden in standard medical practice. Thus, depending on the identification code, the data processing means 50 can refer to a table that defines the type of instrument which matches the identification code of the instrument. Depending on the type, the index time period from the measurement of the geometric properties is then retrieved from a table. The aforesaid index time (expiry time) then can be calculated by means of the index time period and the retrieved time of measurement of the geometric properties. As an alternative or in addition to the code which characterizes the individual medical treatment device, a code also can be retrieved from the RFID transponder 950 that characterizes the type of the instrument, such that it is not necessary to refer to a table within the data processing means 50 that links the identification code and the type of the instrument.

The properties of the data processing means 50 described above also can be realized in the data processing means 400, which can be used to measure the geometric properties of the medical treatment device. In this way, an index time can be determined when measuring the properties of the medical treatment device and written to the RFID transponder of the medical treatment device, as an alternative or in addition to the time of measurement by the measuring device, by means of the RFID writer. In particular, the type of the medical treatment device also can be written to the RFID transponder.

The invention is also directed in particular to the following embodiments, which can be combined with time detection, the RFID writer/reader and storing/reading data in/from the RFID transponder.

A method for examining, in particular for automatically verifying, calibrating or surveying an instrument 700, wherein by means of a scanning unit 100, the geometry of the instrument 700 (including a reference system 800 which is attachable to the instrument 700 and formed by at least two active or passive markers) is detected. By means of a data processing unit 400, a three-dimensional model of the instrument 700 is calculated from the detected information concerning the geometry of the instrument 700 and of the reference system 800. On the basis of the information concerning the geometry of the three-dimensional model of the instrument 700, the instrument 700 is verified, calibrated or surveyed.

The method for automatically verifying, calibrating or surveying an instrument according to the preceding embodiment, wherein the emission characteristics and/or reflection characteristics of the reference system 800 formed from active and/or passive markers are detected from different angles of observation by means of an infrared camera unit 150. From the emission properties and/or reflection properties, the quality or the condition or the shape of the reference system 800 or of individual markers are ascertained by a data processing unit 400 depending on the angle of observation. From this, the optical outline of the reference system is calculated and combined with the ascertained information concerning the geometric outline of the reference system 800.

The method for automatically verifying, calibrating or surveying an instrument 700 according to any one of the preceding embodiments, wherein as a verification or calibration, the geometry of the reference system 800 of the instrument 700 or the geometry of the functional element of the instrument 700, e.g., of the instrument tip 900, is automatically recognized by the scanning unit 100. A data processing unit 400 compares the ascertained geometries with geometries of functional elements and reference systems of other instruments 700, stored in a database; and from the comparison, the information stored for the instrument 700 provided in the scanning device is automatically retrieved from the database.

The method for automatically verifying, calibrating or surveying an instrument 700 according to any one of the preceding embodiments, wherein the surface of the instrument 700 and in particular the reference system 800 and the functional element, e.g., the instrument tip 900, are detected by the scanning unit 100, and the detected information is represented on a display device 300 as a three-dimensional model of the instrument 700, such that the functional element and the reference system of the instrument 700 can be selected by a user by means of a user interface unit 1000.

The method for automatically verifying, calibrating or surveying an instrument 700 according to any one of the preceding embodiments, wherein a rough scan of the instrument 700 is initially carried out by the scanning unit 100. On the basis of the information (obtained by means of the rough scan) concerning the geometry of the instrument 700, a rough structure of the instrument 700 is ascertained. Based on the rough structure of the instrument 700, a comparison is made with instrument data stored in the database, and from the comparison, the information stored for the instrument 700 being examined is retrieved from the database.

The method for automatically verifying, calibrating or surveying an instrument 700 according to any one of the preceding embodiments, wherein as a verification or calibration, and after identifying the instrument 700, the functional elements and the reference system of the instrument 700, in particular their shape and position in relation to each other, are scanned using a fine scan in order to make a precise comparison between the detected information concerning the geometry of the instrument 700 and the information stored in the database concerning the geometry of the instrument 700.

The method for automatically verifying, calibrating or surveying an instrument 700 according to any one of the preceding embodiments, wherein as a verification and if the geometry of the instrument 700 detected by the scanning unit 100 and information concerning the instrument 700 stored in the database deviate within a given tolerance level, the instrument 700 being examined and the instrument 700 stored in the database are assumed to match and a positive verification result is transmitted to the navigation system 600, whereupon the instrument 700 is activated for the subsequent application.

The method for automatically verifying, calibrating or surveying an instrument 700 according to any one of the preceding embodiments, wherein as a calibration and if the geometry of the instrument 700 detected by the scanning unit 100 and information concerning the instrument 700 stored in the database deviate to a larger extent than a given tolerance level, the information, stored in the database of the navigation system 600 concerning the geometry of the instrument 700 is corrected using the ascertained information concerning the geometry of the instrument 700. Alternatively, the instrument 700 is scanned again in the areas of the instrument 700 beyond the tolerance level and the information ascertained by means of the second scanning procedure is transmitted to the database of the navigation system 600.

The method for automatically verifying, calibrating or surveying an instrument 700 according to any one of the preceding embodiments, wherein the instrument 700 is detected by the scanning unit 100 and in particular the distance between the functional element 900 and the reference system 800 is calculated by the data processing unit 400 and transmitted to a navigation system 600 or stored in its database.

The method for automatically verifying, calibrating or surveying an instrument 700 according to any one of the preceding embodiments, wherein as a survey, a rough scan of the instrument 700 and of the reference system 800 is initially carried out. Then, using the detected information, a rough three-dimensional model of the instrument 700 is calculated which is represented on a display device 300. A recognition logic can locate characteristic shapes on the model, in particular geometric shapes forming the reference system 800 or functional elements, and by means of the detected shapes, a scanning area is ascertained within which a new, high-precision scanning procedure is carried out.

The method for automatically verifying, calibrating or surveying an instrument 700 according to any one of the preceding embodiments, wherein the instrument 700 is rotated relative to the scanning unit 100 and the surface of the instrument 700 is detected during the relative rotation. The three-dimensional model of the instrument 700 can be calculated with the aid of the data processing unit 400 from the information concerning the rotation and the ascertained information concerning the surface of the instrument 700.

A method for navigating an instrument 700, wherein once the instrument 700 has been verified, calibrated or surveyed according to any one of the preceding embodiments, the navigation system 600 detects the spatial position of the reference system 800 from the geometric relations of the reference system 800 stored in the database. The navigation system also can determine the spatial position of the functional element 900 of the instrument 700 and can thus also calculate and output to the user its spatial relation to the anatomical structure to be treated.

A computer program is provided which, when running on a computer or loaded onto a computer, carries out the methods according to any one of the preceding embodiments. Also, a program storage medium or computer program product comprising the computer program according to the preceding embodiment.

A device for automatically verifying, calibrating or surveying an instrument 700, comprises
- a scanning unit 100 that can detect the geometry of the instrument 700 and of a reference system 800 relative to the geometry of the instrument 700 (the reference system being attachable to the instrument 700), wherein in particular the instrument 700 can be rotated relative to the scanning unit 100 and
- a data processing unit 400 which, from the detected information concerning the geometry of the instrument 700, in particular the arrangement of the markers forming the reference system 800, can calculate a three-dimensional model and can ascertain the position of the functional element of the instrument 700, in particular automatically, via the characteristic arrangement of the markers of the reference system.

The device for automatically verifying, calibrating or surveying an instrument 700 according to the preceding embodiment, further including an infrared camera unit 150, the spatial position of which with respect to the scanning unit 100 is known or can be determined. The camera unit enables emission characteristics or reflection characteristics of the markers and of the reference system formed by the markers to be determined. From these characteristics, information concerning the condition or the quality or the shape of the markers can be ascertained from various directions of view onto the reference system 800 and combined with the information concerning the geometry of the reference system and stored in a database.

The device for automatically verifying, calibrating or surveying an instrument 700 according to any one of the preceding two embodiments, further comprising a database, wherein the ascertained information concerning the geometry of the instrument 700 including the reference system 800, in particular its distance from the functional element 900 such as for example the tip of the instrument, or concerning the condition or the quality or the shape of the markers can be stored in the database. Alternatively, information concerning the geometry of other instruments, including their reference systems, in particular their distance from the functional element such as for example the tip of other instruments, or concerning the condition or the quality or the shape of the markers of other instruments can be stored in the database.

The device for automatically verifying, calibrating or surveying an instrument 700 according to any one of the preceding three embodiments, further comprising
- a display device 300, in particular a touch screen, on which the ascertained three-dimensional model of the instrument 700 can be represented, and
- a user interface unit 1000 which is arranged in particular on the display device 300, e.g. as a touch screen, by means of which the functional element 900 of the instrument 700, e.g., the instrument tip 900 or the markers forming the reference system (800), can be selected.

The device for automatically verifying, calibrating or surveying an instrument 700 according to any one of the preceding four embodiments, further comprising a navigation system 600 linked wirelessly or via a wire connection to the data processing unit 400 of the scanning device. The ascertained information concerning the instrument, in particular the geometry of the functional element 900 and the reference system 800 and their position in relation to each other, can be transmitted to the navigation system 600. On the basis of the transmitted information concerning the arrangement of the markers forming the reference system, a navigation procedure can be carried out using the navigation system 600 and incorporating and where appropriate compensating for the ascertained errors of the markers.

A device for automatically verifying, calibrating or surveying an instrument 700, used for carrying out the described methods using instruments equipped with a mobile, read-only or readable and writeable data memory which in particular uses wireless transmission technologies such as RFID, in order to provide the identifying features required for the methods describe herein and, where appropriate, in order to store the results on the instrument, after carrying out the methods.

A computer program which automatically determines characteristic geometric structures of the instrument 700, in particular the shape of the functional elements 900 and of the reference system 800 or the markers forming the reference system, with the aid of a recognition algorithm described herein, whereby an identification is possible and the information necessary for automatically verifying, calibrating or surveying the instrument can be retrieved from the database. Automatically recognizing the characteristic geometric structures also can be used to provide suggestions to the user, with the aid of the display device, for the areas to be scanned at a high level of detail.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A measuring device for measuring geometric properties of a medical treatment device, comprising:
   a measuring unit configured to measure a relative position between at least a first part of the medical treatment device and at least a second part of the medical treatment device;
   a time detection unit configured to detect a time of the measurement; and
   an RFID writer configured to write a time, based on the detected time, to an RFID transponder of the medical treatment device.

2. The measuring device according to claim 1, wherein the time based on the detected time is the detected time or is a time calculated from the detected time.

3. The measuring device according to claim 2, wherein the calculated time is calculated based on an index period of time and on the detected time, so as to calculate an index time up to which the geometric properties of the medical treatment device are regarded as being valid.

4. The measuring device according to claim 3, further comprising:
   a data processing device;
   a database communicatively coupled to the data processing device, said database including a plurality of different index periods of time assigned to a plurality of different types of medical treatment devices, and
   wherein the data processing unit, based on the type of the measured medical treatment device, retrieves from the database an index period of time corresponding to the type of instrument, and calculates the index time based on the retrieved index period of time.

5. The measuring device according to claim 1, further comprising a data processing device configured to determine a type of the medical treatment device based on the measured position between the at least first part of the medical treatment device and the at least second part of the medical treatment device.

6. A medical treatment device, comprising:
   a medical instrument; and
   an RFID transponder attached to the medical instrument, the RFID transponder comprising data corresponding to
   i) geometric properties of the medical instrument, said geometric properties including information on a relative position between at least a first part of the medical instrument and at least a second part of the medical instrument and
   ii) a time corresponding to when the geometric properties of the medical instrument were last verified.

7. A method for measuring geometric properties of a medical treatment device, comprising:
   measuring a relative position between a first part of the medical treatment device and a second part of the medical treatment device;
   detecting a time of the measurement of the relative position; and
   storing on an RFID transponder of the medical treatment device a time based on the detected time.

8. A computer program embodied on a non-transitory machine readable medium for measuring geometric properties of a medical treatment device, comprising:
   code that measures from a measurement unit a relative position between a first part of the medical treatment device and a second part of the medical treatment device;
   code that detects from a time detection unit a time of the measurement of the relative position; and
   code that stores on an RFID transponder of the medical treatment device a time based on the detected time.

* * * * *